(12) United States Patent
Maas et al.

(10) Patent No.: US 9,823,241 B2
(45) Date of Patent: Nov. 21, 2017

(54) PROCESSING OF A SAMPLE FLUID WITH TARGET COMPONENTS

(71) Applicant: KONINKLIJKE PHILIPS N.V., Eindhoven (NL)

(72) Inventors: Joost Hubert Maas, Helmond (NL); Wendy Uyen Dittmer, Eindhoven (NL); Mara Johanna Jacoba Sijbers, Helden (NL); Albert Hendrik Jan Immink, Eindhoven (NL); Dominique Maria Bruls, Heeze (NL); Joukje Garrelina Orsel, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/415,085

(22) PCT Filed: Jul. 3, 2013

(86) PCT No.: PCT/IB2013/055442
§ 371 (c)(1),
(2) Date: Jan. 15, 2015

(87) PCT Pub. No.: WO2014/013372
PCT Pub. Date: Jan. 23, 2014

(65) Prior Publication Data
US 2015/0168390 A1 Jun. 18, 2015

Related U.S. Application Data (60) Provisional application No. 61/672,835, filed on Jul. 18, 2012.

(51) Int. Cl.
*G01N 33/543* (2006.01)
*G01N 27/74* (2006.01)
(Continued)

(52) U.S. Cl.
CPC ..... *G01N 33/54333* (2013.01); *G01N 21/253* (2013.01); *G01N 21/552* (2013.01); *G01N 27/745* (2013.01)

(58) Field of Classification Search
CPC .......... G01N 33/54333; G01N 27/745; G01N 21/552; G01N 21/253; G01N 33/54326; G01N 35/0098
See application file for complete search history.

(56) References Cited

U.S. PATENT DOCUMENTS

| 6,699,665 B1* | 3/2004 | Kim | B01L 3/5025 435/288.4 |
|---|---|---|---|
| 2002/0028451 A1 | 3/2002 | Abbott | |

(Continued)

FOREIGN PATENT DOCUMENTS

| WO | 9812539 A1 | 3/1998 |
|---|---|---|
| WO | 2005010542 A2 | 2/2005 |

(Continued)

*Primary Examiner* — Melanie Y Brown (57) ABSTRACT

A cartridge (110) and a method process target components (T1, T2) of a sample fluid, for example the detection of cardiac markers in blood. The cartridge (110) includes a reaction chamber (114) with a hydrophilic reaction surface (115). A physical barrier (116,118) on the reaction surface (115), for example a protrusion, at least partially borders an investigation region (117,117') which includes capture probes (CP1, CP2) that specifically bind to target components (T1, T2) of the sample fluid.

15 Claims, 4 Drawing Sheets

(51) Int. Cl.
*G01N 21/25* (2006.01)
*G01N 21/552* (2014.01)

(56) References Cited

U.S. PATENT DOCUMENTS

| | | |
|---|---|---|
| 2003/0040129 A1 | 2/2003 | Shah |
| 2010/0304359 A1 | 12/2010 | Egan et al. |
| 2012/0147377 A1 | 6/2012 | Schleipen et al. |
| 2012/0220045 A1* | 8/2012 | Bozarth ................ B01L 3/5085 |
| | | 436/174 |
| 2012/0258466 A1* | 10/2012 | Florescu .......... G01N 33/54326 |
| | | 435/7.1 |
| 2014/0080729 A1* | 3/2014 | Grego .................... G01N 21/05 |
| | | 506/9 |

FOREIGN PATENT DOCUMENTS

| | | |
|---|---|---|
| WO | 2005010543 A1 | 2/2005 |
| WO | 2008072156 A2 | 6/2008 |
| WO | 2008115723 A1 | 9/2008 |
| WO | 2008155716 A1 | 12/2008 |
| WO | 2009013668 A2 | 1/2009 |
| WO | 2009016533 A2 | 2/2009 |
| WO | 2009125356 A1 | 10/2009 |
| WO | 2010075632 A1 | 7/2010 |
| WO | 2011027291 A1 | 3/2011 |
| WO | 2011091037 A2 | 7/2011 |
| WO | 2011097412 A1 | 8/2011 |
| WO | 2011097677 A1 | 8/2011 |
| WO | 2011102903 A1 | 8/2011 |

\* cited by examiner

PROCESSING OF A SAMPLE FLUID WITH TARGET COMPONENTS

CROSS-REFERENCE TO PRIOR APPLICATIONS

This application is the U.S. National Phase application under 35 U.S.C. §371 of International Application No. PCT/IN2013/055442, filed Jul. 3, 2013, which claims the benefit of U.S. Provisional Patent Application No. 61/672,835, filed Jul. 18, 2012. These applications are hereby incorporated by reference herein.

FIELD OF THE INVENTION

The invention relates to a cartridge and a method for the processing of a sample fluid with target components. Moreover, it relates to a method for manufacturing such a cartridge and for using such a cartridge.

BACKGROUND OF THE INVENTION

The WO 98/12539 A1 discloses a multi-array, multi-specific electrochemiluminescence testing system in which particular binding domains are made hydrophilic or hydrophobic, while the surrounding surface may have the opposite property (hydrophobic or hydrophilic). Such binding domains are however hard to produce with sufficient precision on a small scale.

Moreover, the WO 2009/125356 A1 discloses a detection apparatus in which protrusions from a detection surface confine the lateral movement of magnetic beads during an assay.

SUMMARY OF THE INVENTION

It is an object of the invention to provide means that allow for the precise and cost-effective processing of sample fluids using reagents like capture probes on a surface.

According to one aspect, the invention relates to a cartridge for the processing of a fluid comprising target components, said fluid being called a "sample fluid" in the following for purposes of reference (without prejudice with respect to its origin or purpose). The "target components" may for example be biological substances like biomolecules, complexes, cell fractions or cells. The "processing" may comprise any kind of e.g. physical or chemical manipulation of the fluid or parts thereof, particularly the qualitative or quantitative detection of the target components. The cartridge comprises the following components:
a) A chamber in which the sample fluid can be provided and which has a surface. For purposes of reference, the chamber will in the following be called "reaction chamber" and the surface "reaction surface". The reaction surface may in general be the complete surface of the reaction chamber, though it will typically be only a part thereof (e.g. the surface that is constituted by one planar wall).
b) At least one region that is located on (or in) the aforementioned reaction surface, that is at least partially bordered by a physical barrier, and that comprises reagents, for example capture probes which can specifically bind to the target components of the fluid. For purposes of reference, this region will in the following be called "investigation region".

The physical barrier usually comprises some solid wall that extends in a direction perpendicular to the reaction surface. It is typically formed by the material of the adjacent body defining the reaction surface. The characteristics of the physical barrier (e.g. its height) are usually such that a confinement of reagents like an antibody solution or magnetic bead solution is achieved only while these are deposited onto the reaction surface (i.e. during cartridge manufacturing), but not during the later assay. In particular, lateral movement of reagents like magnetic particles during an assay shall substantially be unimpeded by the physical barriers.

The mentioned capture probes may for example comprise capture molecules like antibodies that specifically bind to associated antigens. The region that is covered by the capture probes constitutes a "binding area", and it may extend over the whole investigation region or only a part thereof.

The invention further relates to a method for manufacturing a cartridge of the kind described above, said method comprising the following steps:
a) Providing a reaction chamber with a reaction surface and at least one investigation region that is at least partially bordered by a physical barrier.
b) Depositing reagents (e.g. capture probes) in the aforementioned investigation region. The reagents are preferably applied as (or in) a liquid during this deposition step, and later dried.

It was already mentioned that detection is a particularly important example of a "processing" that can be done with the sample fluid. Accordingly, the invention also relates to a method for the detection of target components in a sample fluid, said method comprising the following steps:
a) Introducing the sample fluid into the reaction chamber of a cartridge of the kind described above (with a reaction surface in a reaction chamber and with at least one investigation region that is partially or completely bordered by a physical barrier and comprises one or more binding areas).
b) Detecting target components that are bound to capture probes in the investigation region(s) of the cartridge.

The described cartridges, the method for manufacturing a cartridge, and the method for the detection of target components are related to the same general concept, i.e. the definition of an investigation region on a reaction surface by bordering it with a physical barrier. Explanations and definitions provided for one embodiment of the invention are therefore also valid for the other embodiments, too.

The approach of the present invention has the advantage that it allows for a well localized positioning of reagents like capture probes in an investigation region because the latter is defined by physical barriers, e.g. a protrusion on the reaction surface. This is particularly advantageous as the capture probes are usually applied as liquids which tend to spread over a certain part of the reaction surface, the size of the part depending on the degree of hydrophilicity of the surface, in a more or less controlled manner. The physical barriers also allow to distribute a plurality of investigation regions closer together, making more effective use of the total reaction surface. Moreover, it is for many (optical) applications favorable that the physical barriers can be seen. In an optical detection procedure, the physical barriers can for example very clearly indicate where capture probes are located.

In the following, various preferred embodiments of the invention will be described that relate to the cartridges and the methods described above.

In the method for the detection of target components in the sample fluid, the detection may optionally be done by optical, magnetic, mechanical, acoustic, thermal and/or electrical procedures. A magnetic sensor may for example be provided that comprises a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor may particularly be adapted to detect variations in an output light beam that arise from a frustrated total internal reflection (FTIR) due to target particles at a sensing surface. This approach is described in more detail in the WO 2008/155716 A1, WO 2009/016533A2, or WO 2008/072156 A2.

The physical barrier that at least partially borders the investigation region may particularly comprise a protrusion which constitutes a rim or dike that elevates above the level of the reaction surface and that runs along a (typically line-type) path which completely or partly borders an interior area, the investigation region.

In another embodiment, the physical barrier may comprise a wall of a recess or of an elevation. The investigation region will in this case at least partially be located at the bottom of the recess or at the top or the elevation, respectively.

In a preferred embodiment of the invention, the reaction surface is hydrophilic outside the investigation region. This is often advantageous during the processing of (aqueous) sample fluids as it helps to wet the reaction surface. Inside the investigation region, the reaction surface (below capture probes or other substances deposited in the investigation region) may be hydrophilic or hydrophobic. The first case (hydrophilic) may be advantageous during the deposition of one type of materials, like capture probes for one binding area, onto the investigation region. The later case (hydrophobic) may be advantageous during the deposition of multiple substances like capture probes in the investigation region.

The reaction surface may optionally be located at the surface of a transparent material, for example the surface of a body of glass or transparent plastic. Preferably, the complete body which comprises the reaction chamber may be made from this material. A transparent material allows for optical processing of the sample fluid by light propagating through said material. The reaction surface may be identical to the surface of the transparent material, or it may be separated from this by an intermediate (thin) layer, for example a hydrophilization layer.

The dimensions of the physical barrier which borders the investigation region will typically be chosen in dependence on the thickness of the layer of the liquid containing reagents (e.g. capture probes and/or labels such as magnetic particles) that will be deposited into or onto the investigation region and on the required separation of this layer from the surroundings. Preferably, the physical barrier has a height (above the level of the reaction surface)

higher than about 1 µm and/or lower than about 100 µm, higher than about 2 µm and/or lower than about 80 µm, and/or higher than about 5 µm and/or lower than about 20 µm.

Most preferably, the height ranges at about 10 µm.

Additionally or alternatively, the physical barrier may have a width (measured parallel to the reaction surface) larger than about 2 µm and/or smaller than about 500 µm, larger than about 5 µm and/or smaller than about 400 µm, and/or larger than about 10 µm and/or smaller than about 300 µm.

A typical value ranges at about 20 µm in the case of a line-type protrusion, and at about 200 µm in the case of a two-dimensional elevation or in the case of a two-dimensional recess.

In many embodiments of the invention, the physical barrier may border or surround just one single, connected and uniform area on the reaction surface. In other embodiments of the invention, the investigation region may be divided into two or more sub-regions. Each of these sub-regions may be equipped with different reagents, for example one or more sub-regions with capture probes (constituting "binding areas") and one or more sub-regions with magnetic particles. Other reagents that may be deposited into a (sub-)region can be those that support the intended assay, such as surfactants and preparations that block assay interference. Desired additions depend on the assays that are conducted in the reaction chamber and are well known to persons skilled in the art of assay development.

The aforementioned subdivision of the investigation region may optionally be embodied by one or several physical barriers. However, the sub-regions need not individually be bordered by a physical barrier. A single physical barrier may for example surround one large area into which several antibody spots or the like are deposited, the physical barrier serving to confine another deposited reagent (e.g. a particle solution) in the large area.

In another preferred embodiment, one or more investigation (sub-)regions are equipped with capture probes specific for one analyte (target component), while one or more other investigation (sub-)regions contain capture probes specific for another analyte. Through addition of more investigation regions, yet more different binding areas containing capture molecules with specificities for yet more analytes may be accommodated.

In a following preferred embodiment, multiple investigation regions are equipped with capture probes specific for the same analyte, the capture probes being deposited either in the same or in different concentrations.

In yet another preferred embodiment, capture probes and labels, for example magnetic particles, may be deposited sequentially into the same investigation area, or even deposited simultaneously when provided in the same fluid.

The reaction chamber may preferably comprise two or more investigation regions, wherein each of these investigation regions comprise capture probes that are specific for another target component of the sample fluid. Accordingly, different target components will be processed (e.g. detected) in different investigation regions. This allows for a parallel processing of multiple target components and hence the execution of multiple assays in the same reaction chamber with one sample fluid.

A cartridge according to the present invention may preferably comprise specific capture probes for at least one of the following components: nucleic acids and related compounds (e.g. DNAs, RNAs, oligonucleotides or analogs thereof, oligomerized nucleic acids, polymerized nucleic acids, PCR products, genomic DNA, bacterial artificial chromosomes, plasmids and the like), proteins and related compounds (e.g. polypeptides, peptides, glycoproteins, monoclonal or polyclonal antibodies, soluble or bound receptors, transcription factors, immunoglobulins, hormones, cytokines and the like), small molecules such as antigens, ligands, lipids, drugs, vitamins, hormones, haptens, carbohydrates and related compounds (e.g. polysaccharides, oligosaccharides and the like), cellular fragments such as membrane fragments, cellular organelles, intact cells, bacteria, viruses, protozoa, and the like. Most preferably, two or more of these capture probes are present in different investigation regions of the same cartridge to allow for the parallel processing (detection) of the corresponding target substances. In an embodiment that is particularly useful for the detection of cardiac diseases from a blood sample, the capture probes may bind specific to at least one the following markers: troponin I, myoglobin, B-type natriuretic peptide, and 2,3 C-reactive protein.

In a preferred embodiment of the invention, magnetic particles are added to the sample fluid (before, during, and/or after its introduction into the reaction chamber). The term "magnetic particles" shall comprise both permanently magnetic particles as well as magnetizable particles, for example superparamagnetic beads. The size of the magnetic particles typically ranges between 3 nm and 50 µm. Moreover, the magnetic particles may bind target components one is actually interested in, for example through analyte binding groups that are exposed on their surface. The use of magnetic particles is favorable as they can readily be manipulated with the help of magnetic fields. In a preferred embodiment, magnetic particles are present in one or more investigation areas on the reaction surface before addition of the sample fluid. In another preferred embodiment, magnetic particles are present on the plane of the reaction chamber that is opposite from the reaction surface.

The aforementioned magnetic particles may preferably be confined in a predetermined region, particularly in a volume close to or opposite an associated investigation region by a magnetic field, wherein said confinement may particularly take place during the introduction of the sample fluid into the reaction chamber and/or later on, particularly during assay processing steps in the investigation region. The confinement may be such that the magnetic particles have (almost) no chance to reach another investigation region. In quantitative terms, more than about 90%, preferably more than about 99% of the magnetic particles shall be retained in the associated investigation region. Accordingly, the amount of magnetic particles at the particular investigation region has a constant, known value. Furthermore, different types of magnetic particles (e.g. particles of different sizes and/or coated with different binding molecules) may be used in different investigation regions without a risk of undesired cross reactions. The magnetic confinement may for example be achieved by a magnet disposed below the investigation region.

During introduction of the sample fluid into the reaction chamber, the magnetic particles may particularly be attracted so firmly to the investigation region or opposite plane that they are not hydrodynamically distributed in the sample fluid. To this end, a magnetic field gradient of sufficient strength and directed to the surface supporting the magnetic particles may be applied, for example with the help of a magnet arranged below the reaction surface (if the magnetic particles are in the investigation region) or above the reaction surface (if the magnetic particles are in the plane opposite to the investigation region).

When the mentioned magnetic particles are already in the cartridge prior to the addition of the sample fluid, they may be disposed at and/or in the investigation region. This is particularly useful if there are different investigation regions which shall be provided with different types of magnetic particles. In this case, the corresponding magnetic particles can be located from the beginning at/in their associated investigation region.

Additionally or alternatively, magnetic particles may be provided on another surface of the reaction chamber than the reaction surface. If the cartridge is for example composed of a body with an open chamber (comprising the reaction surface) and a cover closing said chamber, the magnetic particles may be disposed on the interior surface of the cover. This embodiment is particularly favorable if the same type of magnetic particles shall be distributed within the whole sample fluid.

When the reaction chamber comprises two or more investigation regions, the same or a different type of magnetic particle may be deposited in some (or in each) of these regions. Accordingly, it will be possible to perform assays based on different magnetic particles in these investigation regions.

The invention further relates to the use of a cartridge of the kind described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules. Most preferably, the use comprises the detection of diseases, for example cardiac diseases.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

The invention will in the following be explained with respect to biosensors for the detection of specific components in body fluids like saliva, urine, blood, wherein the biosensors make use of magnetic particles (beads) covered with capture probes. Specific magnetic actuation schemes may be applied in these biosensors to optimize the assay performance. The presence of target molecules in the sample may be detected by the degree of binding of magnetic beads to a detection spot or "binding area", i.e. to areas which are covered with specific capture molecules or probes. The presence of magnetic beads bound to the investigation region inside, as well as outside of, the binding areas, may for example be detected by optical means.

In the specific example of cardiac application, a biosensor may use a finger prick blood sample for the quantitative detection of a number of biomarkers that are indicative for the occurrence of a myocardial infarct. The biosensor can be used in a point-of-care setting (emergency room, bedside, ambulance, physician's office or even at home). Several important cardiac marker proteins have been identified and may be used in the clinical practice. For example, troponin I may be used as a standard biomarker based on its absolute cardiac specificity and its long serum half-life. A fast increase of myoglobin level in bloodstream following heart attack may enable a rapid patient stratification. B-type natriuretic peptide may be useful for the emergency diagnosis of heart failure and for the prognosis in patients with acute coronary syndromes. 2,3 C-reactive protein is an important prognostic indicator of coronary heart disease and acute coronary syndromes.

A simultaneous quantification of such cardiac markers allows clinicians to diagnose coronary heart disease quickly and to accurately design a patient care strategy. A fast and reliable detection of a panel of cardiac markers will help medical professionals to differentiate between patients showing similar symptoms. Different markers are present in different diagnostically relevant concentrations and can require different assay conditions for an optimal lower limit of detection and dynamic range.

It is therefore desirable to have a cartridge for a biosensor in which different markers can be measured at the same time in one reaction chamber. This can be achieved by a spatial separation of the antibodies and the magnetic beads corresponding to the specific assays so that cross reactivity effects are avoided and multiple assays can be carried out.

The problem which is addressed by the present invention therefore concerns the integration of multiple assay spots in one reaction chamber. For simultaneous quantification of e.g. multi-cardiac-markers an individual assay format needs to be expanded to multi-analyte detection.

One method for multi-analyte biosensing would be using multiple labels. However, a loss of sensitivity in the multi-analyte format is usually observed, compared to the individual assay format, due to the poor discrimination of signals generated by distinct labels. The present invention therefore proposes to use an antibody array format where different antibodies specific for each of the targeted analytes are immobilized in discrete areas in one single reaction chamber by incorporating physical barriers in the reaction chamber. One advantage of this approach is the separation of functions of the different areas in the reaction chamber.

Figure 1:
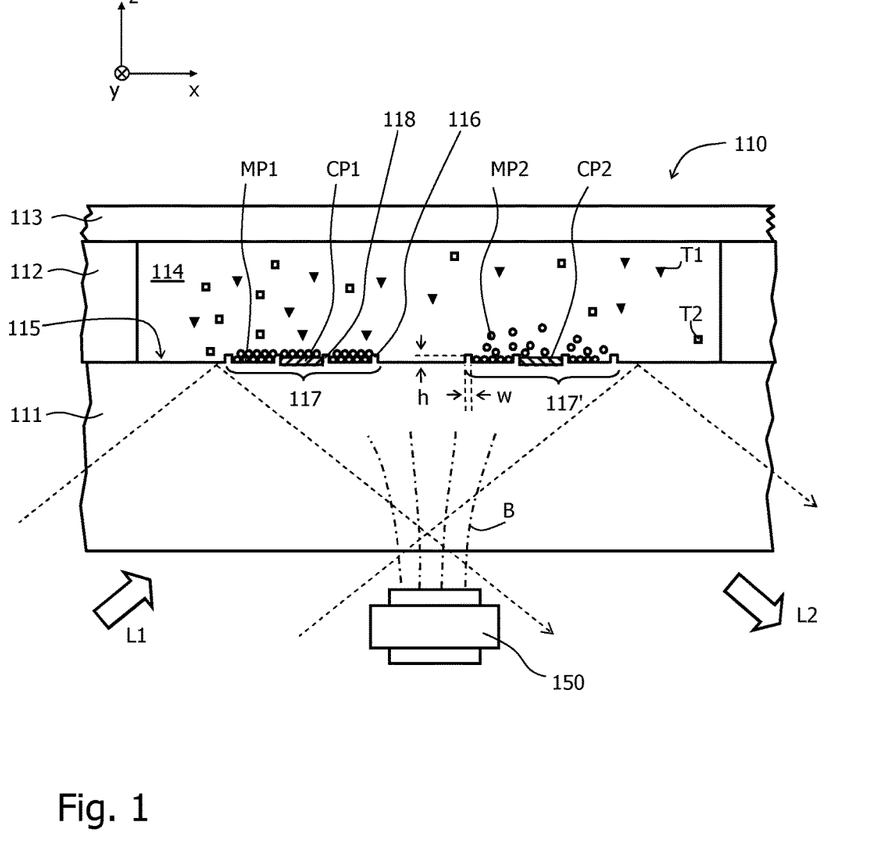
FIG. 1 schematically shows a side view of a cartridge according to the present invention in which the physical barriers around the investigation regions are formed by protrusions.

FIG. 1 schematically shows a section through a cartridge 110 according to one exemplary embodiment of the present invention. The cartridge 110 is used for the detection of target components T1, T2 comprised in a sample fluid (e.g. blood) that fills a reaction chamber 114 of the cartridge. The cartridge 110 is composed of a transparent base part 111 which borders the reaction chamber 114 at its bottom side and which provides a reaction surface 115. The side walls of the reaction chamber 114 are constituted by an intermediate layer 112, for example a tape into which openings for the reaction chamber and associated fluidic channels (not shown) have been cut. The reaction chamber 114 is covered at its top side by a (plastic) cover 113. Alternatively, the reaction chamber can be formed by a recess in the bottom and/or top part. Of course many other designs of the reaction chamber are possible, too.

Several investigation regions 117, 117' are formed on the reaction surface 115. Each investigation region 117, 117' is geometrically defined by protrusions 116, 118 serving as physical barriers that confine areas filled with reagents for the associated investigation region. In the shown example, the reagents particularly comprise capture probes CP1, CP2 located in a disk-shaped central "binding area" that is surrounded by a circular protrusion 118. Moreover, magnetic particles MP1, MP2 are deposited in the larger area that comprises the aforementioned binding area and that is bordered by an outer protrusion 116. The protrusions 116, 118 may for example have a height h of about 10 μm and a width w of about 20 μm.

The bindings sites CP1, CP2 may particularly be antibodies that are applied for example by ink-jetting and bound to the underlying substrate. The protrusion 118 around this area keeps the antibody spot solution, and thus the resulting antibody spot, confined to the dedicated area during the production of the cartridge. After drying and washing the excess material may be removed. The volume of the deposited magnetic beads MP1, MP2 is larger than that of the capture probes, and therefore the corresponding ring-shaped area is bigger than the central binding area. Usually, the magnetic particles MP1, MP2 are deposited on top of the spot of capture probes.

Hydrophilization of the reaction surface 115 is possible to get good hydrophilic properties. Optionally, one can choose to not hydrophilize the total reaction surface, but use the physical barriers 116, 118 to confine hydrophilization to the areas outside of the physical barriers. This enables spotting of capture probes CP1, CP2 onto hydrophobic surfaces, in case they bind better to these surfaces than to hydrophilic surfaces.

Figure 2:
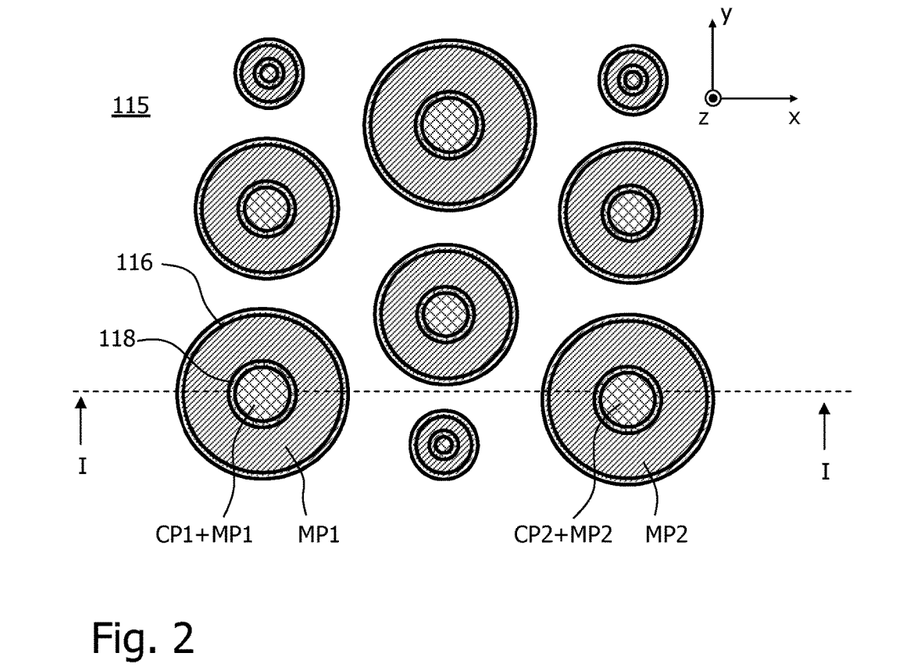
FIG. 2 shows a top view onto the reaction surface of the cartridge of FIG. 1.

FIG. 2 shows in a top view onto the reaction surface 115 that a plurality of investigation regions of the kind described above are spread across the reaction surface 115, wherein the investigation regions may have different shapes and/or diameters (as shown), or all have the same shape and/or diameter.

In FIG. 1, the magnetic particles MP1 of the left investigation region 117 are shown in a still aggregated state that is assumed before the introduction of a sample fluid into the reaction chamber 114 (and immediately thereafter). At the right investigation region 117', some of the magnetic particles MP2 have already dissolved in the adjacent volume of the sample fluid.

FIG. 1 further shows a magnetic field generator, for example an electromagnet 150, for generating a magnetic field B in the reaction chamber 114 by which the magnetic particles MP1, MP2 of the investigation regions can be manipulated. In particular, it is possible to attract the magnetic particles firmly to the reaction surface 115 during the filling of the reaction chamber 114 with a sample fluid such that they are prevented from spreading all over the whole reaction chamber. The filling of the reaction chamber (i.e. the time between applying the sample and the complete filling of the reaction chamber with sample) may for example last between about 1 s and 120 s, preferably between about 5 s and 60 s.

The filling of the cartridge is typically followed by an incubation period to allow for analyte capture by the magnetic particles. Thereafter, the magnetic field B may be used to actuate the magnetic particles in order to optimize their selective binding to their associated investigation region (e.g. magnetic particles MP1 to a volume at investigation region 117). It was observed that during this actuation, minimal lateral spreading of the magnetic particles occurs, such that cross reactions between different investigation regions are also minimal. The average strength of the magnetic field gradient during the filling of the reaction chamber will typically be stronger than during the following period (e.g. the period of incubation), for example by a factor of about 2, most preferably a factor of about 10. It is also possible to apply a magnetic field (gradient) during the filling of the reaction chamber but not during the ensuing incubation period (zero gradient).

It should be noted that the magnetic field generator may optionally comprise other or further magnets, for example a magnet on the opposite side of the cartridge 110. The electromagnet 150 may preferably be a horseshoe-magnet with two poles arranged behind each other in y-direction.

FIG. 1 further indicates an input light beam L1 that is totally internally reflected at the reaction surface 115 and then leaves the cartridge 110 as an output light beam L2 towards a light detector (not shown). These light beams can be used to detect target components of the sample fluid that are specifically bound to magnetic particles MP1, MP2 and the capture probes CP1, CP2 of the investigation regions 117, 117'. Further details of this assay and the optical detection of target components by frustrated total internal reflection (FTIR) may be found for example in the WO 2008/115723 A1, which is incorporated into the present text by reference.

The base part 111 of the cartridge is preferably made of injection molded plastic (e.g. polystyrene, polycarbonate, COP, COC, ABS etc). The proposed physical barriers 116, 118 may for example be produced by focused ion beam processes or femto-second laser ablation in the mould, but many variations can be conceived for the preparation of the physical barriers.

In the described example, separate areas or sub-regions are provided in each investigation region for the antibodies CP1, CP2 and magnetic beads MP1, MP2, respectively. In another embodiment of the invention, magnetic particles may be deposited not on the reaction surface but on the cover 113 (laminate). In this case one only needs the small disk-shaped areas to deposit the antibodies.

This results in an array format where different antibodies specific for each of the targeted analytes are immobilized in discrete areas. Simultaneous assays can be used in fully integrated systems, leading to simultaneous multiple determinations in a single drop of blood.

Figure 3:
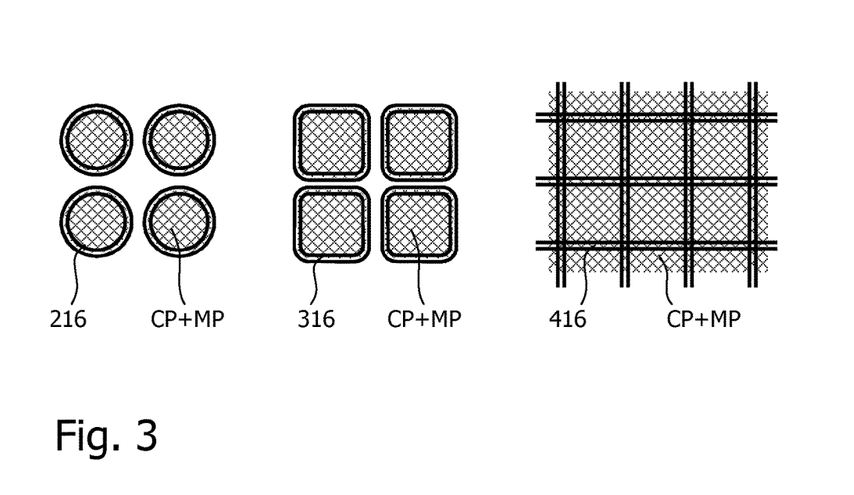
FIG. 3 shows a top view onto alternative embodiments of reaction surfaces for the cartridge of FIG. 1.

FIG. 3 schematically shows a top view onto alternative embodiments of reaction surfaces for a cartridge like that of FIG. 1.

In the left part of FIG. 3, several investigation regions of identical circular shape are formed by circular protrusions 216 that surround a single, connected region. This region may be covered with reagents such as for example capture probes CP, magnetic particles MP or other reagents or any combination of reagents.

In the central part of FIG. 3, several investigation regions are formed by protrusions 316 that surround a single, connected region having a square (or rectangular) shape with rounded corners. Again, the regions may be covered with reagents such as for example capture probes CP, magnetic particles MP or other reagents or any combination of reagents.

In the right part of FIG. 3, the protrusions 416 constitute a rectangular grid on the reaction surface. The cells of this grid are investigation regions that may be covered with reagents such as for example capture probes CP, magnetic particles MP or other reagents or any combination of reagents.

Figure 4:
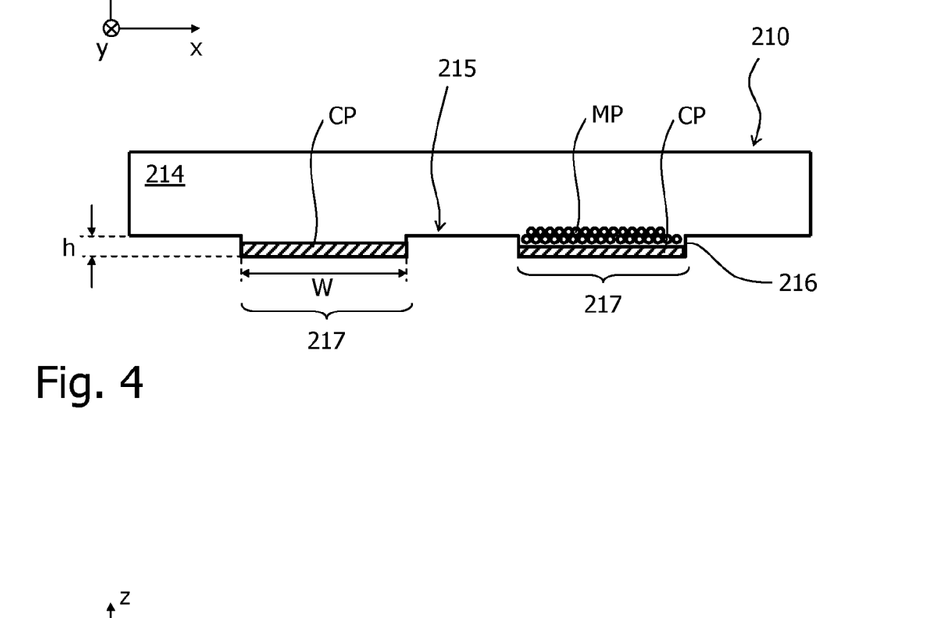
FIG. 4 schematically shows a side view of a cartridge in which the physical barriers around the investigation regions are formed by walls of recesses.

FIG. 4 schematically illustrates a cartridge 210 according to another embodiment of the invention. The cartridge 210 comprises a reaction chamber 214 with a reaction surface 215 in which several investigation regions 217 are located. These investigation regions 217 are bordered by physical barriers in the form of the walls 216 of a recess, said walls having a height h (the width of the barrier being approximately zero). The investigation regions 217 themselves are located at the bottom of these recesses. The recesses have a width W between about 50 µm and about 300 µm. As above, the investigation regions may be filled with reagents, in particular with capture probes CP and/or magnetic particles MP.

Figure 5:
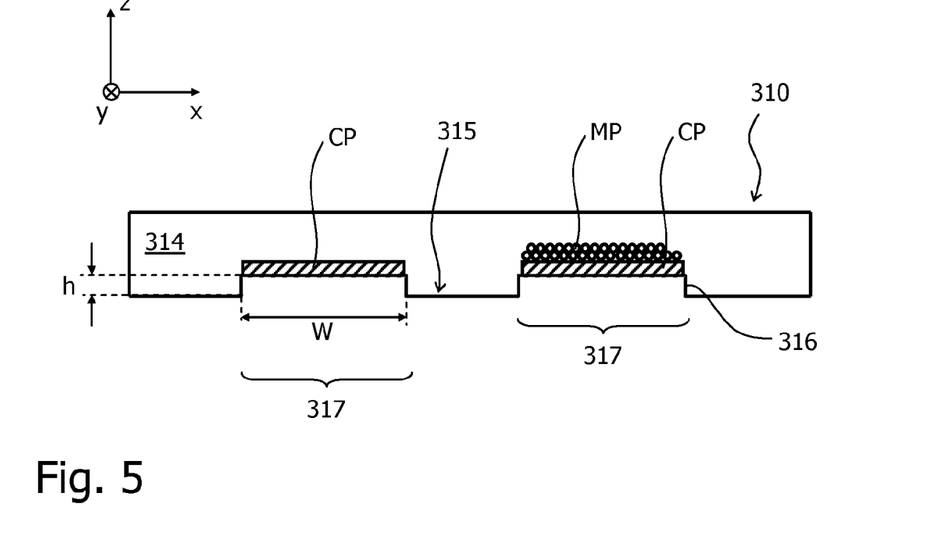
FIG. 5 schematically shows a side view of a cartridge in which the physical barriers around the investigation regions are formed by walls of elevations.

FIG. 5 schematically illustrates a cartridge 310 according to still another embodiment of the invention. The cartridge 310 comprises a reaction chamber 314 with a reaction surface 315 in which several investigation regions 317 are located. These investigation regions 317 are bordered by physical barriers in the form of the walls 316 of an elevation or pillar, said walls having a height h (the width of the barrier being approximately zero). The investigation regions 317 themselves are located at the top of these pillars. The pillars have a width W between about 50 µm and about 300 µm. As above, reagents may be deposited in the investigation regions, in particular capture probes CP and/or magnetic particles MP.

The walls 216 and 316 in FIGS. 4 and 5 serve as physical barriers in the same manner as the protrusions 116, 118 in FIG. 1 do. Explanations provided with respect to the protrusions are therefore analogously valid for the walls 216 and 316, too. For example, the height of the walls 216 and 316 may typically have a height h of about 10 µm.

Figure 6:
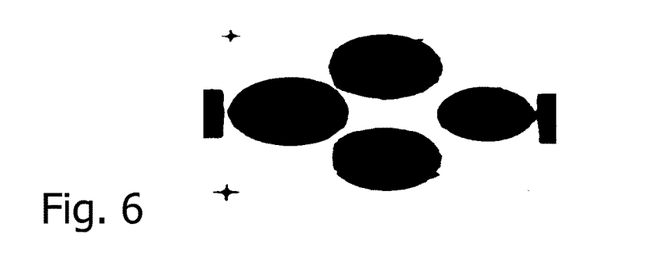
FIG. 6 shows four investigation regions with magnetic particles before the filling of the reaction chamber.
Figure 7:
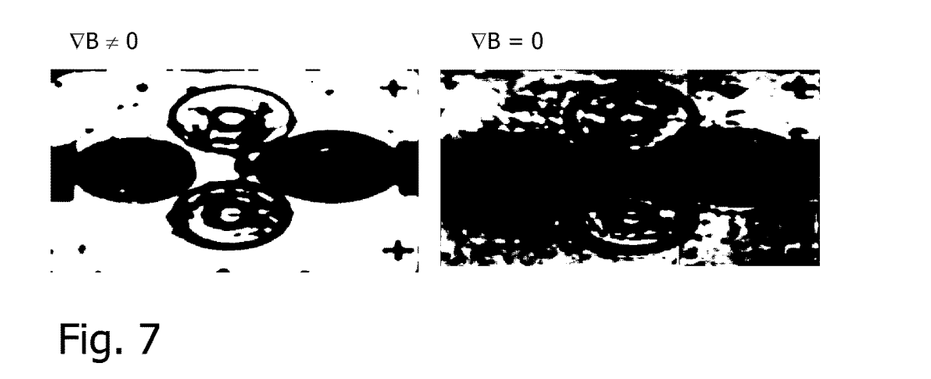
FIG. 7 shows said four investigation regions after the filling of the reaction chamber when magnetic particles were held down by a magnetic field gradient (left) or not (right)
Figure 8:
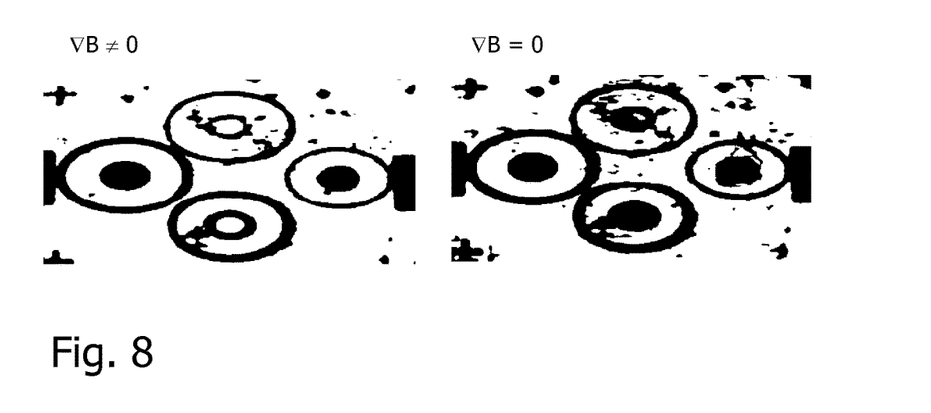
FIG. 8 shows four investigation regions after binding when magnetic particles were confined to their investigation region by a magnetic field gradient (left) or not (right) during the filling of the reaction chamber.

FIGS. 6-8 show photographs of a reaction surface with four investigation regions that are designed with concentric protrusions as shown in FIG. 2. The images illustrate the effect of the magnetic confinement during cartridge filling. In the associated experiments, capture probes (antibodies) were deposited in the inner protrusions of the investigation regions, and magnetic particles were deposited on top of these capture probes, also covering the area within the outer protrusions.

FIG. 6 shows the investigation regions before introduction of a sample. Deposited magnetic particles are visible (black color) in FTIR. All magnetic particles are well located inside their associated investigation region.

During cartridge filling the magnetic particles were pulled towards the reaction surface by an appropriate magnetic field gradient ∇B using the electromagnets below the cartridge (left images in FIG. 7, 8) or not (right images in FIG. 7, 8). After that, a standard assay was performed (incubation without magnetic actuation, then binding with magnetic actuation, then magnetic wash).

The images of FIG. 7 were taken during the binding phase. It is clear that the magnetic pulling during cartridge filling has kept the magnetic particles quite well in the location of their own protrusions (investigation regions), while without magnetic pulling they spread out much more over the reaction surface. An advantage of the magnetic confinement during filling is that the bead concentration above the investigation region is kept quite high. In the state of the art, magnetic beads are deposited above the whole reaction chamber. When they are deposited inside the protrusions of the investigation regions, much less volume is available and less beads can be deposited. With the help of the magnetic confinement during filling, the beads remain concentrated above the investigation region and good assay signals can still be obtained even when smaller numbers of beads are deposited.

Another advantage of the magnetic hold-down step is that the magnetic beads can be kept quite well separated, reducing interference with other beads and investigation regions within the same chamber and thus facilitating multiplexed detection. This is illustrated by the measurement of FIG. 8. Above the top and bottom investigation regions, non-functional magnetic particles were deposited, while the magnetic particles deposited above the left and right investigation regions were functional (i.e. provided with capture sites for target molecules). With the magnetic confinement during filling (left image), functional magnetic particles do not migrate to and bind to the top and bottom investigation regions, evidenced by the lack of signal there. Without the magnetic hold down step, particle binding is observed at the top and bottom investigation regions, too, indicating that functional particles moved there from the left and right spots.

In summary, the present invention is related to a cartridge in which different markers can be measured at the same time in one reaction chamber. Due to the local separation of the antibodies and the magnetic beads corresponding to that specific assay cross reactivity effects are avoided and multiple assays conditions can be carried out.

The invention can for example be applied in multiplex assays, which simultaneously measure multiple analytes in a single measurement. They are widely used in functional genomics experiments, proteomics, inkjet printers, blood-cell-separation equipment, biochemical assays, chemical synthesis, genetic analysis, drug screening, and the immediate point-of-care diagnosis of diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A cartridge for the detection of target components (T1, T2) in a sample fluid with magnetic particles (MP1, MP2, MP), comprising:
   a reaction chamber in which the sample fluid can be provided and which has a reaction surface;
   at least one investigation region that is located on the reaction surface and is at least partially bordered by a physical barrier;
   wherein the investigation region is subdivided into two concentric subregions;
   wherein reagents that specifically bind to target components are deposited in one of the subregions and the magnetic particles are deposited in the other subregion;
   wherein the reaction surface is hydrophilic outside the investigation region;
   a magnetic field generator for generating a magnetic field (B) that confines the magnetic particles (MP1, MP2, MP) at an associated investigation region during introduction of the sample fluid into the reaction chamber;
   an optical, magnetic, mechanical, acoustic, thermal or electrical sensor unit for the detection of target components (T1, T2) in the investigation region;
   wherein the physical barrier has a height (h) of 1 μm to 100 μm and a width (w) of 2 μm to 500 μm and is configured not to impede a lateral movement of the magnetic particles (MP1, MP2, MP).

2. A cartridge for the processing of a sample fluid with target components (T1, T2), comprising:
   a reaction chamber in which the sample fluid can be provided and which has a reaction surface;
   at least one investigation region that is located on the reaction surface, is at least partially bordered by a physical barrier, and comprises reagents, for example capture probes (CP1, CP2), that specifically bind target components (T1, T2) of the sample fluid;
   wherein the reaction surface is hydrophilic outside the investigation region;
   wherein the physical barrier has a height (h) of 1 μm to 100 μm and a width (w) of 2 μm to 500 μM and is configured not to impede a lateral movement of the magnetic particles (MP1, MP2, MP); and
   wherein the investigation region is divided into two concentric subregions, the reagents being deposited in one of the subregions and the magnetic particles being deposited in the other.

3. A method for manufacturing a cartridge according to claim 1, said method comprising the following steps:
   providing a reaction chamber with a reaction surface and with at least one investigation region that is at least partially bordered by a physical barrier, the investigation region being subdivided into concentric subregions;
   wherein the reaction surface is hydrophilic outside the investigation region; and wherein the physical barrier has a height (h) of 1 μm to 100 μm and a width (w) of 2 μm to 500 μm and is configured not to impede a lateral movement of the magnetic particles (MP1, MP2, MP); and
   depositing reagents like capture probes (CP1, CP2) in the one of the subregions.

4. A method for the detection of target components (T1, T2) in a sample fluid, said method comprising the following steps:
   introducing the sample fluid into the reaction chamber of a cartridge according to claim 1;
   detecting target components (T1, T2) bound to capture probes (CP1, CP2) in the investigation region.

5. The method according to claim 4, wherein the detection is done by an optical, magnetic, mechanical, acoustic, thermal or electrical procedure.

6. The cartridge according to claim 1, wherein the physical barrier comprises a protrusion and/or a wall of a recess or an elevation.

7. The cartridge according to claim 1, wherein the reaction surface is hydrophobic inside the investigation region.

8. The cartridge according to claim 1, wherein the reagents include capture probes (CP1, CP2, CP) which specifically bind to at least one of nucleic acids, proteins, antigens, ligands, lipids, drugs, vitamins, hormones, haptens, carbohydrates, cellular fragments, and related compounds, including troponin I, myoglobin, B-type natriuretic peptide, and/or 2,3 C-reactive protein.

9. The cartridge according to claim 1, wherein the magnetic particles (MP1, MP2, MP) are added to the sample fluid.

10. The cartridge according to claim 8, wherein the magnetic particles (MP1, MP2, MP) are confined in the other of the subregions by the magnetic field (B).

11. The cartridge according to claim 8, wherein the magnetic particles (MP1, MP2, MP) are disposed in the other of the subregions.

12. The cartridge according to claim 1, wherein the reaction chamber comprises at least two subregions
   with different capture probes (CP1, CP2) that are specific for different target components (T1, T2) and/or
   with different types of magnetic particles (MP1, MP2).

13. The cartridge according to claim 1, wherein the physical barrier has a height (h) of about 10 μm.

14. The cartridge according to claim 13, wherein the physical barrier has a width (w) of about 20 μm.

15. A cartridge for detection of target components (T1, T2) in a sample fluid with magnetic particles (MP1, MP2, MP), comprising:
   a reaction chamber in which the sample fluid can be provided and which has a reaction surface;
   at least one investigation region that is located on the reaction surface and is at least partially bordered by a physical barrier;
   wherein the reaction surface is hydrophilic outside the investigation region;
   a magnetic field generator for generating a magnetic field (B) that confines the magnetic particles (MP1, MP2, MP) at an associated investigation region during introduction of the sample fluid into the reaction chamber;
   an optical, magnetic, mechanical, acoustic, thermal or electrical sensor unit for the detection of target components (T1, T2) in the investigation region;
   wherein the physical barrier has a height (h) of 1 μm to 100 μm and a width (w) of 2 to 500 μm and is configured not to impede a lateral movement of the magnetic particles (MP1, MP2, MP),
   wherein the at least one investigation region includes first and second concentric subregions and wherein a portion of the physical barrier is disposed between the subregions, surrounding the inner subregion and another portion of the physical barrier surrounds an outer of the concentric subregions;
   wherein reagents that specifically bind to target components are deposited in at least one of the subregions.

* * * * *